United States Patent

Augeri et al.

(10) Patent No.: US 10,221,133 B2
(45) Date of Patent: Mar. 5, 2019

(54) (THIO, OXO, AND SELENO) SEMICARBAZONE COMPLEXES WITH ZINC AND THEIR USE FOR TREATING CANCER

(71) Applicants: RUTGERS, THE STATE UNIVERSITY OF NEW JERSEY, New Brunswick, NJ (US); THE RESEARCH FOUNDATION FOR THE STATE UNIVERSITY OF NEW YORK, Syracuse, NY (US)

(72) Inventors: David J. Augeri, New Brunswick, NJ (US); Anthony F. Bencivenga, New Brunswick, NJ (US); Adam Blanden, Syracuse, NY (US); Darren R. Carpizo, New Brunswick, NJ (US); John A. Gilleran, New Brunswick, NJ (US); Spencer David Kimball, New Brunswick, NJ (US); Stewart N. Loh, Syracuse, NY (US); Xin Yu, New Brunswick, NJ (US)

(73) Assignees: Rutgers, The State University of New Jersey, New Brunswick, NJ (US); The Research Foundation for the State University of New York, Syracuse, NY (US)

(*) Notice: Subject to any disclaimer, the term of this patent is extended or adjusted under 35 U.S.C. 154(b) by 0 days.

(21) Appl. No.: 15/545,966

(22) PCT Filed: Jan. 27, 2016

(86) PCT No.: PCT/US2016/015183
§ 371 (c)(1),
(2) Date: Jul. 24, 2017

(87) PCT Pub. No.: WO2016/123246
PCT Pub. Date: Aug. 4, 2016

(65) Prior Publication Data
US 2018/0002279 A1   Jan. 4, 2018

Related U.S. Application Data

(60) Provisional application No. 62/108,415, filed on Jan. 27, 2015, provisional application No. 62/258,177, filed on Nov. 20, 2015.

(51) Int. Cl.

| | |
|---|---|
| A61K 31/175 | (2006.01) |
| A61K 31/315 | (2006.01) |
| A61K 31/397 | (2006.01) |
| C07D 205/04 | (2006.01) |
| C07D 213/53 | (2006.01) |
| C07D 401/12 | (2006.01) |
| C07C 281/08 | (2006.01) |
| C07C 337/08 | (2006.01) |

(52) U.S. Cl.
CPC .......... *C07C 337/08* (2013.01); *A61K 31/175* (2013.01); *A61K 31/315* (2013.01); *A61K 31/397* (2013.01); *C07C 281/08* (2013.01); *C07D 205/04* (2013.01); *C07D 213/53* (2013.01); *C07D 401/12* (2013.01)

(58) Field of Classification Search
None
See application file for complete search history.

(56) References Cited

U.S. PATENT DOCUMENTS

| | | | |
|---|---|---|---|
| 4,665,173 A | 5/1987 | Klayman et al. | |
| 2013/0345164 A1 | 12/2013 | Vazquez et al. | |
| 2014/0142266 A1 | 5/2014 | Sakamoto et al. | |
| 2018/0000772 A1 | 1/2018 | Augeri et al. | |
| 2018/0000806 A1 | 1/2018 | Augeri et al. | |
| 2018/0002280 A1 | 1/2018 | Augeri et al. | |

FOREIGN PATENT DOCUMENTS

| | | |
|---|---|---|
| WO | 2001094340 A1 | 12/2001 |
| WO | 2006019955 A2 | 2/2006 |
| WO | 2006101740 A2 | 9/2006 |
| WO | 2007035489 A2 | 3/2007 |
| WO | 2009039553 A1 | 4/2009 |
| WO | 2012175962 A1 | 12/2012 |

(Continued)

OTHER PUBLICATIONS

Todorovic et al, Inorganic Chemistry Communications, vol. 9, No. 8, pp. 862-865 (Year: 2006).*
Mohan et al, Journal of Inorganic Biochemistry, vol. 34, No. 1, pp. 41-54 (Year: 1988).*
Webster et al, Journal of the American Chemical Society, vol. 95, No. 19, pp. 6505-6506 (Year: 1973).*
Agrawal, et al., "Potential antitumor agents. 13. 4-Methyl-5-amino-1-formylisoquinoline thiosemicarbazone", Journal of Medicinal Chemistry 19(7), 970-972 (1976).
Antonini, et al., "Elucidation of the structure of the antineoplastic agents, 2-formylpyridine and 1-formylisoquinoline thiosemicarbazones", Journal of Medicinal Chemistry 20(3), 447-449 (1977).

(Continued)

*Primary Examiner* — Zinna Northington Davis
(74) *Attorney, Agent, or Firm* — Viksnins Harris Padys Malen LLP (57) ABSTRACT

The invention provides organic complexes of $Zn^{2+}$ of formula (I) that are useful for treating cancer, as well as compositions and kits comprising such complexes, and intermediate monomer compounds that are useful for the preparation of such complexes.

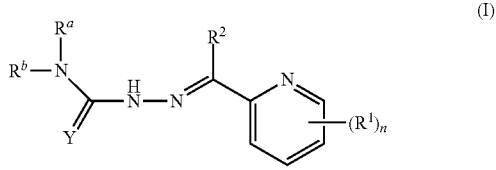

11 Claims, 5 Drawing Sheets

(56) References Cited

FOREIGN PATENT DOCUMENTS

| WO | 2015021456 A1 | 2/2015 |
| WO | 2016123242 A1 | 8/2016 |
| WO | 2016123250 A1 | 8/2016 |
| WO | 2016123253 A1 | 8/2016 |

OTHER PUBLICATIONS

Bellitto, et al., "Conformational Studies of Some Potentially Bidentate Thiosemicarba-zones and Related Complexes of Zinc(II)", J.C.S. Dalton 68570(21), 758-762 (1976).

Chun-Ying, et al., "Synthesis, Crystal Structure and Nonlinear Optical Properties of Thiosemicarbazone Zinc Complex", J Coord Chem 47, 433-439 (1999).

Easmon, et al., "2-benzoxazolyl and 2-benzimidazolyl hydrazones derived from 2-acetylpyridine: a novel class of antitumor agents", Int J Cancer 94, 89-96 (2001).

Easmon, et al., "Synthesis, Structure-Activity Relationships, and Antitumor Studies of 2-Benzoxazolyl Hydrazones Derived from Alpha-(N)-acyl Heteroaromatics", J Med Chem 49, 6343-6350 (2006).

Easmon, et al., "Thiazolyl and benzothiazolyl hydrazones derived from α-(N)-acetylpyridines and diazines: synthesis, antiproliferative activity and CoMFA studies", Eur J Med Chem 32, 397-408 (1997).

File Caplus, "Preparation and characterization of vanillin thiosemicarbazone complexes with cobalt(II), nickel(II), copper(II), zinc(II), cadmium(II), and mercury(II)", STN CA Caesar Accession No. 1170, 2 pages (1984).

File Caplus, "Synthesis and crystal structure of zinc(II) complex [Zn(25-MBTSC)2I2]", STN CA Caesar Accession No. 1162, 1 page (2013).

File Caplus, "Synthesis and structure of 1.5Zn(phen)3.cntdot.L. cntdot..3N03 supramolecule (phen=o-phenanthroline, L=4-aminoacetophenone thiosemicarbazone", STN CA Caesar Accession No. 1176, 2 pages (2008).

Hall, et al., "Investigations on the Mechanism of Action of the Novel Antitumor Agents 2-Benzothiazolyl, 2-Benzoxazolyl, and 2-Benzimidazolyl Hydrazones Derived from 2-Acetylpyridine", Arch Pharm Pharm Med Chem 332 (4), 115-123 (1999).

Huang, et al., "A Series of α-Heterocyclic Carboxaldehyde Thiosemicarbazones Inhibit Topoisomerase IIα Catalytic Activity", Journal of Medicinal Chemistry 53, 3048-3064 (2010).

Huang, et al., "Correlating gene expression with chemical scaffolds of cytotoxic agents: ellipticines as substrates and inhibitors of MDR1", Pharmacogenomics Journal 5, 112-125 (2005).

Ibrahim, et al., "Indole-7-carbaldehyde thiosemicarbazone as a flexidentate ligand toward ZnII, CdII, PdII and PtII ions: cytotoxic and apoptosis-inducing properties of the PtII complex", Dalton Trans 43, 3860-3860 (2014).

Kalinowski, et al., "Design, Synthesis, and Characterization of Novel Iron Chelators: Structure-Activity Relationships of the 2-Benzoylpyridine Thiosemicarbazone Series and Their 3-Nitrobenzoyl Analogues as Potent Antitumor Agents", Journal of Medicinal Chemistry 50(15), 3716-3729 (2007).

Khalaji, et al., "Synthesis and Characterization of Zinc(II) Complexes with 3,4-Dimethoxybenzaldehyde Thiosemicarbazone: The Crystal Structure of [Zn(34-MBTSC) 2 Cl 2 ]", Phosphorus, Sulfur, and Silicon 188, 1119-1126 (2013).

Kovala-Demertzi, et al., "Zinc(II) complexes derived from pyridine-2-carbaldehyde thiosemicarbazone and (1E)-1-pyridin-2-ylethan-1-one thiosemicarbazone. Synthesis, crystal structures and antiproliferative activity of zinc(II) complexes", Journal of Inorganic Biochemistry 100, 1558-1567 (2006).

Moorthy, et al., "QSAR analysis of 2-benzoxazolyl hydrazone derivatives for anticancer activity and its possible target prediction", Med Chem Res 21, 133-144 (2012).

Mrozek-Wilczkiewicz, et al., "Iron Chelators in Photodynamic Therapy Revisited: Synergistic Effect by Novel Highly Active Thiosemicarbazones", ACS Medicinal Chemistry Letters 5(4), 336-339 (2014).

Patent Cooperation Treaty, International Searching Authority, Search Report and Written Opinion for PCT/US2016/015183, 13 pages, dated Mar. 30, 2016.

Priyadharsini, et al., "Docking, synthesis, characterization and evaluation of novel cdk2 inhibitors: benzothiazole derivatives", International Journal of Pharmacy and Pharmaceutical Sciences 4(3), 574-585 (2012).

Ren, et al., "A new approach to suppress nonlinearity-transparency trade-off through coordination chemistry: syntheses and spectroscopic study on second-order nonlinear optical properties of a series of square-pyramidal zinc (II) complexes", Spectrochimica Acta Part A 59, 1095-1101 (2003).

Richardson, et al., "Dipyridyl Thiosemicarbazone Chelators with Potent and Selective Antitumor Activity Form Iron Complexes with Redox Activity", J Med Chem 49, 6510-6521 (2006).

Ruangpornvisuti, et al., "A DFT investigation of conformational geometries and interconversion equilibria of phenylthiosemicarbazone and its complexation with zinc", J Mol Model 10, 418-426 (2004).

Sleebs, et al., "Discovery of Potent and Selective Benzothiazole Hydrazone Inhibitors of Bcl-XL", J Med Chem 56, 5514-5540 (2013).

Tian, et al., "Structural characterization and second-order nonlinear optical properties of zinc halide thiosemicarbazone complexes", Polyhedron 21, 1217-1222 (2002).

Yu, et al., "Allele-Specific p53 Mutant Reactivation", Cancer Cell 21, 614-625 (2012).

Yu, et al., "Small molecule restoration of wildtype structure and function of mutant p53 using a novel zinc-metallochaperone based mechanism", Oncotarget 5(19), 8879-8892 (2014).

* cited by examiner

(THIO, OXO, AND SELENO) SEMICARBAZONE COMPLEXES WITH ZINC AND THEIR USE FOR TREATING CANCER

CROSS-REFERENCE TO RELATED APPLICATIONS

This patent application claims the benefit of priority of U.S. application Ser. No. 62/108,415, filed Jan. 27, 2015, and of U.S. application Ser. No. 62/258,177, filed Nov. 20, 2015, which applications are herein incorporated by reference.

FIELD

The disclosure relates to organic complexes of zinc and their use in the treatment of cancer.

BACKGROUND OF THE INVENTION

TP53 is the most commonly mutated gene in human cancer for which no effective targeted anti-cancer drug exists. The majority of TP53 mutations (>70%) are missense mutations that generate a defective protein that is generally found at high levels in cancer cells due to loss of MDM2 negative feedback. Restoring the function of p53 in mouse models of cancer is highly therapeutic. Reactivating mutant p53 using small molecules has been highly sought after, yet remains an elusive goal in the development of cancer therapeutics.

SUMMARY OF THE INVENTION

This invention provides novel complexes, kits, and methods directed toward refolding TP53 mutant proteins into their wild-type conformations by treatment with zinc(II) metallochaperone complexes.

More specifically, one aspect of the present invention provides a complex comprising $Zn^{2+}$ and a compound of formula (I):

or an ion or poly-ion thereof, wherein:
n is 0, 1, 2, 3, or 4;
Y is O, S, or Se;
each $R^1$ is independently selected from $(C_1-C_4)$alkyl, $(C_1-C_4)$alkoxy, hydroxyl, and halo;
$R^2$ is selected from the group consisting of H and $(C_1-C_6)$alkyl that is optionally substituted with aryl; and
$R^a$ and each $R^b$ are each independently selected from H, $(C_1-C_6)$alkyl, aryl, and aryl$(C_1-C_6)$alkyl; or $R^a$ and each $R^b$ taken together with the nitrogen to which they are attached form a heterocycle that is optionally substituted with one to three substituents independently selected from $(C_1-C_4)$alkyl, $(C_1-C_4)$alkoxy, hydroxyl, halo, aryl, and heteroaryl.

Another aspect of the invention provides a complex of zinc and a metallochaperone wherein the ratio of the number of compounds of formula (I) to zinc $Zn^{2+}$ ions is about 2:1.

Another aspect of the invention provides a complex of formula:

or a solvate thereof.

Another aspect of the present invention provides a pharmaceutical composition, comprising a complex of a compound of formula I and a pharmaceutically acceptable carrier.

Another aspect of the present invention provides a method of inhibiting cancer cell growth, comprising contacting the cancer cell with an effective amount of a compound of formula I or a salt thereof.

Another aspect of the present invention provides a method of treating cancer in an animal (e.g. a human), comprising administering to the animal a compound of formula I or a pharmaceutically acceptable salt thereof.

The invention further includes methods of preparing, methods of separating, and methods of purifying the compounds described herein.

Additional advantages and novel features of this invention shall be set forth in part in the description that follows, and in part will become apparent to those skilled in the art upon examination of the following specification, or may be learned by the practice of the invention.

The advantages of the invention may be realized and attained by means of the instrumentalities, combinations, compositions, and methods particularly pointed out in the appended claims.

DESCRIPTION OF THE INVENTION

The following definitions are used, unless otherwise described: halo is fluoro, chloro, bromo, or iodo. Alkyl, alkoxy, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1$-$C_4)$ alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

The term allyl as used herein refers to a substituent, molecular fragment, or radical having the chemical formula —$CH_2$—CH=$CH_2$.

The term "benzyl" as used herein refers to a substituent, molecular fragment, or radical having the chemical formula —$CH_2C_6H_5$.

The term "butyl" as used herein refers to a four-carbon alkyl radical, substituent, or molecular fragment having the chemical formula —$C_4H_9$.

The term "cyclopropyl" as used herein refers to a radical, substituent, or molecular fragment having a chemical structure derived from cyclopropane and having the chemical formula $C_3H_5$.

The term "ethyl" as used herein refers to an alkyl substituent, radical, or molecular fragment having the chemical formula —$C_2H_5$.

The term "heterocycle" as used herein includes 4-, 5-, and 6-membered rings containing one or more heteroatoms selected from N, O, and S. In one embodiment, heterocycle includes azetidino, pyrrolidino, and piperidino.

The term "isopropyl" as used herein refers to a propyl with a group attached to the secondary carbon.

The term "methyl" as used herein refers to an alkyl derived from methane and containing one carbon atom bonded to three hydrogen atoms and having the chemical formula —$CH_3$.

The term "propyl" as used herein refers to a linear three-carbon alkyl substituent, molecular fragment, or radical having the chemical formula —$C_3H_7$.

The term "phenyl" refers to a cyclic group of atoms, radical, substituent, or molecular fragment having the chemical formula —$C_6H_5$.

The term "ion" refers to a compound bearing a charge. The term poly-ion refers to a compound bearing more than one charge (e.g. two charges). For example, an ion of a compound of formula (I) can be prepared by deprotonating a compound of formula (I) to provide the corresponding ion of the compound of formula (I) that bears a −1 charge. Similarly, an poly-ion (e.g. a dianion) of a compound of formula (I) can be prepared by deprotonating a compound of formula (I) to provide the corresponding poly-ion of the compound of formula (I) that bears, for example, a −2 charge. Ions of the compounds of formula (I) may be incorporated into the complexes of the invention.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1$-$C_6)$alkyl can be methyl, ethyl, propyl, isopropyl, butyl, iso-butyl, sec-butyl, pentyl, 3-pentyl, or hexyl; $(C_1$-$C_6)$alkoxy can be methoxy, ethoxy, propoxy, isopropoxy, butoxy, iso-butoxy, sec-butoxy, pentoxy, 3-pentoxy, or hexyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

In one embodiment, $R^a$ and $R^b$ taken together with the nitrogen to which they are attached form a 4-, 5-, or 6-membered heterocycle that is optionally substituted with one to three substituents independently selected from $(C_1$-$C_4)$alkyl, $(C_1$-$C_4)$alkoxy, hydroxyl, halo, aryl, and heteroaryl. In another embodiment, $R^a$ and $R^b$ taken together with the nitrogen to which they are attached form an azetidino, pyrrolidino, or piperidino ring that is optionally substituted with one to three substituents independently selected from $(C_1$-$C_4)$alkyl, $(C_1$-$C_4)$alkoxy, hydroxyl, halo, aryl, and heteroaryl.

In one embodiment, the complexes of the invention have a $K_d$ $Zn^{2+}$ in the range from about 1 nM-500 nM.

In one embodiment, the complexes of the invention have a $K_d$ $Zn^{2+}$ in the range from about 10-200 nM.

The ability of ZMCl, NTA ($Zn^{2+}$-binding homolog), and A6 (Example 10) to increase intracellular $[Zn^{2+}]_{free}$ was evaluated by treating cells with the fluorescent $Zn^{2+}$ indicator FluoZin-3-AM (FZ3-AM) in complete media and imaging them using confocal microscopy. In both HEK293 (non-cancer, p53-WT) and TOV112D (ovarian cancer, p53-R175H) cells, ZMCl increased intracellular $[Zn^{2+}]_{free}$ as indicated by increased fluorescence, but NTA and A6 did not. This result is consistent with the metallochaperone (MC) model for ZMC1 function and explains the inability of NTA and A6 to reactivate p53-R175H at micromolar concentrations.

ZMC1 (6)

A6 (10)

NTA

To determine whether ZMC1 is an ionophore the fluorescent $Zn^{2+}$ indicator RhodZin-3 (RZ-3) was encapsulated inside 1,2-dioleoyl-sn-glycero-3-phosphocholine (DOPC) liposomes; the ability to transport $Zn^{2+}$ in and out was monitored by fluorescence. $Zn^{2+}$ alone was unable to permeate the liposomal membrane as indicated by the lack of RZ-3 fluorescence increase. Addition of ZMC1 caused a dose-dependent increase in the rate of RZ-3 fluorescence increase, indicating that ZMC1 can facilitate the transport of $Zn^{2+}$ into the liposomes.

Of the two control compounds, A6 (Example 10) shuttled $Zn^{2+}$ into the liposomes, but NTA did not. NTA binds $Zn^{2+}$ with an affinity similar to that of ZMC1, but it cannot cross either liposomal or cellular membranes, likely because it possesses negative charges. A6, on the other hand, lacks charges and is similar in structure to ZMC1, but binds $Zn^{2+}$ weakly ($K_d$=1.1 µM). It can function as an ionophore in conditions of the liposome experiments where external $[Zn^{2+}]_{free}$ was 10 µM. However, in complete media containing 10% fetal bovine serum (FBS), $Zn^{2+}$-binding proteins from the serum (e.g. albumin) necessarily compete for $Zn^{2+}$ with any putative MC, making the effective $[Zn^{2+}]_{free}$ much lower than $[Zn^{2+}]_{total}$. A6 therefore likely does not increase intracellular $[Zn^{2+}]_{free}$ in culture because $K_{d,A6}$ is greater than extracellular $[Zn^{2+}]_{free}$. Thus, both an appropriate $Zn^{2+}$ $K_d$ and ionophore activity influence ZMC1 activity.

To determine whether ZMC1 can traverse lipid bilayers as a free compound, the $[Zn^{2+}]_{free}$ gradient was reversed by adding a large excess of metal ion chelator EDTA to the solution outside of the liposomes; fluorescence was monitored in the presence and absence of ZMC1. EDTA alone did not cause a significant decrease in RZ-3 fluorescence as the liposomal membranes are impermeable to EDTA. After subsequent addition of ZMC1, there was a time dependent decrease in RZ-3 fluorescence. This result indicates that free ZMC1 crossed the liposomal membranes, bound internal $Zn^{2+}$, and transported it back outside the liposome where the metal was then bound by the much stronger chelator EDTA. Thus, ZMC1 can cross biological membranes both as free drug and drug-$Zn^{2+}$ complex, and therefore can transport $Zn^{2+}$ into cells without becoming trapped as either species.

To ensure that the fluorescence results were due to $Zn^{2+}$ transport and not to non-specific disruption of liposomal membranes, a liposomal leakage assay was performed using the self-quenching fluorophore calcein. When calcein is encapsulated at concentrations above 4 mM its fluorescence is decreased via self-quenching. Leakage is detected by a fluorescence increase as the dye dilutes and its fluorescence dequenches. At the highest concentrations of ZMC1 and $ZnCl_2$ a significant fluorescence increase was not detected. Disruption of liposomes can also be detected by alteration of their size distribution. The size distribution of liposomes treated with the highest concentrations of $ZnCl_2$ and ZMC1 was identical to that of untreated liposomes. Together, these data indicate the liposomal membranes remained intact upon ZMC1 treatment, and therefore the RZ-3 fluorescence changes are attributable only to specific $Zn^{2+}$ transport.

Characterization of ZMC1-Mediated $Zn^{2+}$ Transport in Live Cells

To extend the investigation of ZMC1 as an ionophore to living systems, ZMC1-mediated $Zn^{2+}$ transport was quantified in cells. The kinetics of intracellular $[Zn^{2+}]_{free}$ increase was measured by loading HEK293 and TOV112D cells with FZ3-AM, treating the cells with ZMC1 and $ZnCl_2$, and monitoring fluorescence by time-lapse microscopy. To minimize the potential for $Zn^{2+}$ contamination and contributions from poorly defined elements in complete media (e.g. FBS), cells were treated and imaged in $Ca^{2+}$ and $Mg^{2+}$-free Earle's Balanced Salt Solution supplemented with 10 mM HEPES pH 7.4 (EBSS/H (−)Ca/Mg). Excess $ZnCl_2$ with the $Zn^{2+}$ ionophore pyrithione (PYR) was used as a positive control. Excess membrane-permeable $Zn^{2+}$ chelator N,N,N',N'-tetrakis(2-pyridylmethyl)ethane-1,2-diamine (TPEN) was used as a negative control. When treated with $ZnCl_2$ alone or ZMC1 alone, neither cell type showed an increase in intracellular $[Zn^{2+}]_{free}$. When treated with both ZMC1 and $ZnCl_2$, both cell lines showed a time dependent increase at two different $ZnCl_2$ concentrations, demonstrating that both ZMC1 and extracellular $Zn^{2+}$ are required. When the fluorescence increases were fit to first-order exponentials, both concentrations of $ZnCl_2$ yielded identical half-lives in their respective cell types, which we combine to report $t_{1/2}$ (HEK293)=124±20 s and $t_{1/2}$ (TOV112D)=156±50 s (mean±SD, n=4).

The steady-state intracellular $[Zn^{2+}]_{free}$ of both cell types was then quantified after treatment with the 2:1 ratio of ZMC1:$ZnCl_2$. Cells were again loaded with FZ3-AM, treated with 1 µM ZMC1 and 0.5 µM $ZnCl_2$ in EBSS/H (−)Ca/Mg, and imaged as above. To normalize for differential dye loading, cells were then sequentially treated with excess PYR/$ZnCl_2$, imaged, treated with TPEN, and imaged again. PYR/$ZnCl_2$ and TPEN served to saturate and apoize the intracellular FZ3, respectively. In the absence of drug an intracellular $[Zn^{2+}]_{free}$ of 0.69±0.25 nM was measured for HEK293 cells and 0.71±0.19 nM was measured for TOV112D cells. These values reflect the lower limit of detection by FZ3-AM and are likely overestimates. Upon treatment with ZMC1 and $ZnCl_2$ intracellular $[Zn^{2+}]_{free}$ rose to 18.1±4.7 nM for HEK293 cells and 15.8±2.5 nM for TOV112D cells. These concentrations are theoretically sufficient to reactivate ~90% of p53-R175H based on the $K_{d1}$ value of 2.1 nM measured for DBD-R175H.

Materials and Methods

Reagents

FZ3-AM, RZ-3 ($K^+$ salt), and cell culture media were purchased from Life Technologies. DOPC was purchased from Avanti Polar Lipids. ZMC1 and A6 were similarly obtained. $Zn^{2+}$(ZMC1)$_2$ was synthesized and crystallized. HEK293 and TOV112D cells were purchased from ATCC and maintained in DMEM+GlutaMAX with 10% FBS and 1 mg/mL penicillin-streptomycin under a 5% $CO_2$ atmosphere at 37° C. All non-cell based experiments were conducted in 50 mM Tris pH 7.2, 0.1 M NaCl at 25° C.

Liposome Import Assay

DOPC-liposomes were prepared by film rehydration and extrusion followed by gel filtration and diluted to an $OD_{600}=0.06$ in buffer. The size distribution of the liposomes was determined by dynamic light scattering (DLS) using a Malvern Zetasizer Nano ZS. Fluorescence measurements were taken on a Horiba Fluoromax-4 spectrofluorimeter in a 5×5 mm quartz cuvette with $\lambda_{ex}/\lambda_{em}=550/572$ nm for RZ-3 and 490/515 nm for calcein. Initial $Zn^{2+}$ import/export was quantified by fitting the first 10-30 s of data after each treatment to a line and converted to units of flux using the following Eqn 1:

$$J_i = \frac{\Delta F}{\Delta t} \cdot \left(\frac{F_{max} - F_{min}}{[RZ3]}\right) \cdot \left(\frac{SA}{Vol}\right) \quad \text{Eqn 1}$$

where $J_i$ is the initial flux, $\Delta F/\Delta t$ is the slope of the fit line, $F_{max}$ is RZ-3 fluorescence in the presence of saturating $Zn^{2+}$ and 1% TritonX-100, $F_{min}$ is RZ-3 fluorescence in the presence of excess EDTA and 1% TritonX-100, [RZ3] is the concentration of encapsulated RZ-3, and SA/Vol is the surface area to volume ratio calculated assuming hollow spheres of the mean diameter determined by DLS.

Intracellular $[Zn^{2+}]_{free}$ Imaging

TOV112D or HEK293 cells (40,000 cells/well) were plated on either 8-well BD Falcon chambered culture slides (Corning Life Sciences) or 8-chambered #1.5 Nunc Lab-Tek II chambered coverglasses (Thermo Scientific) treated with poly-L-lysine. After 48 h, cells were washed 2×5 m in serum-free media and incubated with 1 μM FZ3-AM for 40 m at 37° C. Cells were then washed 2×5 m in either EBSS/H (−)Ca/Mg or phenol-red free DMEM+10% FBS containing the indicated treatments for 20 m before imaging. For nuclear colocalization, 1 μg/mL Hoechst 33342 was also included. Cells were imaged using a Zeiss LSM510 META NLO confocal microscope equipped with 37° C. environmental control chamber. FZ3 and Hoechst 33342 were excited at 488 nm (argon laser) and 790 nm (Chameleon Ti:sapphire laser), respectively. To determine the kinetics of fluorescence change, each background-subtracted image in the time-lapse series was integrated in ImageJ and normalized to the integrated fluorescence of the first frame after treatment. For quantification of intracellular $[Zn^{2+}]_{free}$, each cell was analyzed in the treated, 50 μM PYR/ZnCl$_2$ (1:1), and 100 μM TPEN images by taking the mean fluorescence of an ROI inside the cell subtracted by an ROI immediately outside the cell measured in ImageJ. The $[Zn^{2+}]_{free}$ for each cell was then calculated by Eqn 2:

$$[Zn^{2+}]_{free} = \frac{F - F_{min}}{F_{max} - F} \cdot K_d \quad \text{Eqn 2}$$

Where F, $F_{max}$, and $F_{min}$ are fluorescence in the treatment, PYR/ZnCl$_2$, and TPEN images, respectively, and $K_d$ is that of FZ3 for $Zn^{2+}$ (15 nM). To minimize the effects of outliers the lowest and highest 5% of cells in each series were rejected, and the remaining values averaged to give the value from that experiment. The number of cells analyzed in each trial ranged from 54-163. For nuclear colocalization, treated, PYR/ZnCl$_2$, and TPEN treated images costained with Hoechst 33342 were aligned and each pixel subjected to Eqn. 2 in MATLAB (MathWorks). The resultant images were Gaussian mean filtered and false-colored by calculated $[Zn^{2+}]_{free}$.

p53-R175H Immunofluorescence

DMEM+10% FBS was treated with 5 g Chelex 100 resin per 100 mL media for 1 hour with gentle shaking. The media was then decanted and filtered through 0.2 μm sterile filter. TOV112D cells were then incubated with 1 μM ZMCl in untreated media, Chelex-treated media, or media+10 μM TPEN at 37° C. for 2 h, fixed, and stained with PAB240 and PAB1640.

Figure 2:
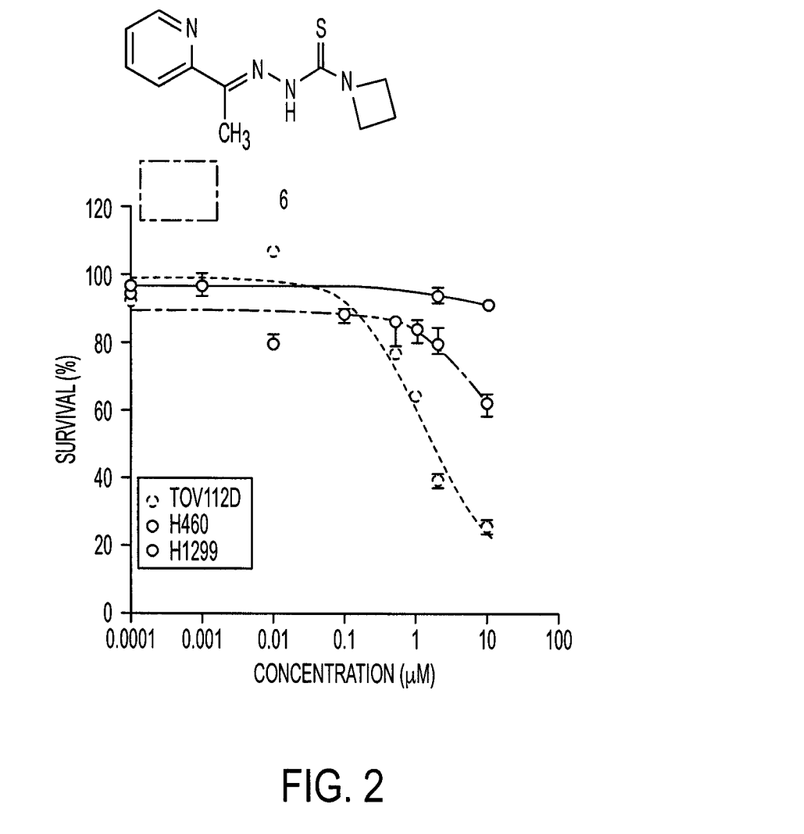
FIG. 2 illustrates the three day cell growth inhibition assays comparing three human tumor cell lines, TOV112D (p53-R175H), H460 (p53-WT), and H1299 (p53-null) for compound 6.

Assays:

Cell growth inhibition assay using human tumor cell lines with different p53 status (wildtype, null, p53-R175H) were employed to determine if wildtype structure is restored to mutant p53 after treatment with a zinc metallochaperone. Compound 6 shown in FIG. 2 selectively killed the p53-R175H tumor cell line (TOV112D) while leaving the p53 wildtype (H460) and p53 null (H1299) cell lines undisturbed.

Figure 3:
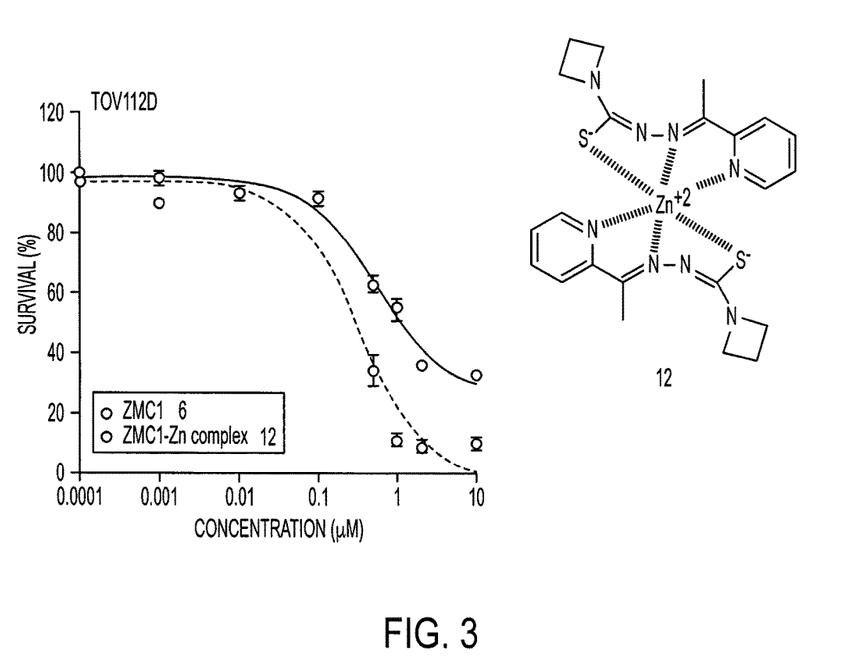
FIG. 3 shows the superiority of the Zinc (II) complex 12 over the monomeric form 6 (ZMCl) in vitro: Zinc (II) complex 12 exhibits greater potency over monomeric form 6 (ZMCl). A cell growth inhibition assay was performed with 12 using monomer 6 as a control. Note the increased potency of the complex with tumor cell death approaching 100 percent.

When assayed side-by-side, the Zn (II) complex 12 exhibited greater potency in the TOV112D (p53-R175H) cells than the monomers 6 alone, FIG. 3.

Figure 4:
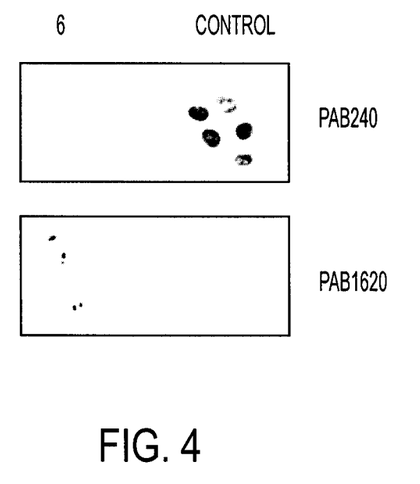
FIG. 4 shows PAB1620 antibody recognition of wildtype conformation after treatment of mutant p53 with compound 6.

An immunofluorescence assay using conformation specific antibodies was used to determine if a test compound could induce a wildtype conformation of mutant p53. The results illustrated in FIG. 4 show PAB1620 antibody recognition of wildtype conformation after treatment of mutant p53 with compound 6. Compound 6 causes mutant p53 to refold into the wildtype conformation forcing cells to pro-apoptotic endpoint.

The invention will now be illustrated by the following non-limiting Examples.

EXAMPLES

Chemistry: General Method A.

A general synthetic approach to the preparation thiosemicarbazone monomers is shown in Example 2.

Chemistry: General Method B for the synthesis of the [Zn(thiosemicarbazone)$_2$] complexes.

Figure 1:
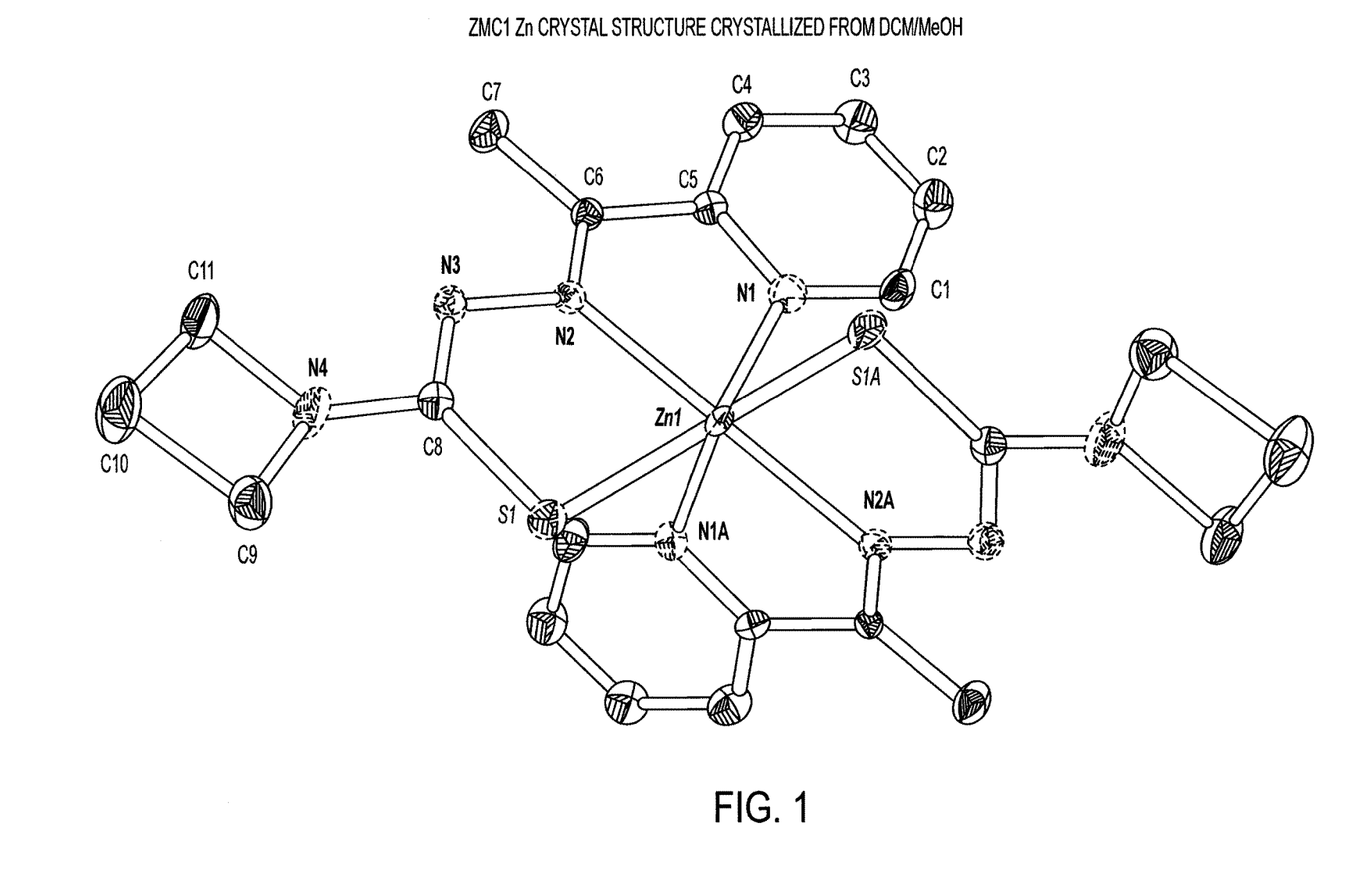
FIG. 1 shows the X-ray structure of compound 12 (ZMCl Zn); ORTEP drawing from X-ray crystallographic data.

A general synthetic approach to the preparation small molecule complexes with Zn (II) is shown in Scheme 1. Treatment of 6 with 0.5 equiv. of ZnCl$_2$ and excess triethylamine in ethanol heated to reflux for 2 hours afforded, after cooling to ambient temperature, the crystalline complex 12 (Kovala-Demertzi, D., Yadav, P. N., Wiecek, J., Skoulika, S., Varadinova, T., and Demertzis, M. A. (2006) Zn(II) complexes derived from pyridine-2-carbaldehyde thiosemicarbazone and (1E)-1-pyridin-2-ylethan-1-one thiosemicarbazone. Synthesis, crystal structures and antiproliferative activity of Zn(II) complexes. *Journal of Inorganic Biochemistry* 100, 1558-1567). Recrystallization from the appropriate solvent afforded crystals suitable for X-ray crystallographic analysis. In each case, the protocol gave the complex with 2:1 stoichiometry where two monomers were deprotonated to form a complex with Zn with an overall neutral charge. FIG. 1 shows the ORTEP drawing of the X-ray structure of compound 12.

Scheme 1

ZMC1 (6)

0.5 eq ZnCl$_2$, TEA, EtOH
reflux 2 h 7.61 (E/Z d, J=7.68 Hz, 1H), 8.40 and 8.66 (E/Z br. s, 1H, NH), 8.46 and 8.55 (E/Z d, J=3.76 Hz, 1H). MS: 248.9 [M+H]⁺.

Example 3

(E)-N-methyl-N'-(1-(pyridin-2-yl)ethylidene)azetidine-1-carbothiohydrazide (3)

Following General Method A for the condensation of N-methylazetidine-1-carbothiohydrazide and 1-(pyridin-2-yl)ethan-1-one the title compound 3 was isolated as a yellow solid after recrystallization from EtOAc/Hex. ¹H-NMR (400 MHz, CDCl₃) δ 2.10 (t, J=7.76 Hz, 1H), 2.14 (t, J=7.80 Hz, 1H), 2.48 (s, 3H), 3.56 (s, 3H), 4.18 (t, J=7.72 Hz, 4H), 7.38 (ddd, J=5.92 Hz, 4.80 Hz, 1.08 Hz, 1H), 7.76 Hz (dt, J=7.76 Hz, 1.76 Hz, 1H), 8.10 (d, J=8.04 Hz, 1H), 8.66 (m, 1H). MS: 248.9 [M+H]⁺.

Example 4

(E)-2-(1-(pyridin-2-yl)ethylidene)hydrazine-1-carbothioamide (4)

Following General Method A for the condensation of hydrazinecarbothioamide and 1-(pyridin-2-yl)ethan-1-one the title compound 4 was isolated as a white solid after recrystallization from MeOH. ¹H-NMR (400 MHz, DMSO-d₆) δ 2.39 (s, 3H), 7.38 (dd, J=7.24 Hz, 5.76 Hz, 1H), 7.79 (dt, J=9.17 Hz, 1.68 Hz, 1H), 8.13 (br. s, 1H, NH), 8.39 (br. s, 1H, NH), 8.43 (d, J=8.08 Hz, 1H), 8.58 (d, J=4.08 Hz, 1H), 10.30 (s, 1H, NH).

Example 5

(12)

Example 1

(E)-N'-(1-(6-methylpyridin-2-yl)ethylidene)azetidine-1-carbothiohydrazide (1). General Method A To a solution of azetidine-1-carbothiohydrazide (156 mg, 1.19 mmol, 1.0 eq) and 1-(pyridin-2-yl)ethan-1-one (152 mg, 1.25 mmol, 1.05 eq) in DCM (6 ml) was added AcOH (4 drops). After stirring overnight at room temperature, the reaction was concentrated under reduced pressure and recrystallized from MeOH to afford 1 as a crystalline white solid (132 mg, 0.56 mmol, 47%). ¹H-NMR (400 MHz, CDCl₃) δ 2.35 (m, 5H), 2.56 and 2.67 (E/Z s, 3H), 4.34 (m, 2H), 4.70 (m, 2H), 7.11 and 7.18 (E/Z d, J=7.52 Hz, 1H), 7.30 and 7.65 (E/Z d, J=8.00 Hz, 1H), 7.56 and 7.73 (E/Z t, J=7.84 Hz, 1H), 8.71 (s, 1H, NH). MS: 248.9 [M+H]⁺.

Example 2

(E)-N'-(1-(3-methylpyridin-2-yl)ethylidene)azetidine-1-carbothiohydrazide (2)

Following General Method A for the condensation of azetidine-1-carbothiohydrazide and 1-(3-methylpyridin-2-yl)ethan-1-one the title compound 2 was isolated as a white solid after recrystallization from MeOH. ¹H-NMR (400 MHz, CDCl₃) δ 2.27 (m, 6H), 2.43 (m, 2H), 4.37 (m, 4H), 7.19 and 7.26 (E/Z dd, J=7.72 Hz, 4.72 Hz, 1H), 7.56 and (E)-4-(pyridin-2-yl)-N'-(1-(pyridin-2-yl)ethylidene) piperazine-1-carbothiohydrazide (5)

Following General Method A for the condensation of 4-(pyridin-2-yl)piperazine-1-carbothiohydrazide and 1-(pyridin-2-yl)ethan-1-one the title compound 5 was isolated as a white solid after recrystallization from MeOH. $^1$H-NMR (400 MHz, DMSO-d$_6$) δ 2.41 and 2.68 (E/Z s, 3H), 3.57 (t, J=5.28 Hz, 2H), 3.66 (t, J=5.30 Hz, 2H), 4.03 (t, J=4.80, 2H), 4.12 (m, 2H), 6.68 (app t, J=4.88 Hz, 1H), 6.85 (app. t, J=8.72 Hz, 1H), 7.40 and 7.57 (E/Z m, 1H), 7.57 (m, 1H), 7.84 and 8.03 (E/Z t, J=7.72 Hz, 1.72 Hz, 1H), 7.92 and 8.04 (E/Z d, J=7.88 Hz, 1H), 8.14 (m, 1H), 8.61 and 8.76 (E/Z d, J=4.16 Hz, 1H), 10.00 and 14.81 (E/Z s, 1H, NH). MS: 341.1 [M+H]$^+$.

Example 6

(E)-N'-(1-(pyridin-2-yl)ethylidene)azetidine-1-carbothiohydrazide (6)

Following General Method A for the condensation of azetidine-1-carbothiohydrazide and 1-(pyridin-2-yl)ethan-1-one the title compound 6 was isolated as a white solid after recrystallization from MeOH. $^1$H-NMR (400 MHz, DMSO-d$_6$) δ 2.26 (m, 2H), 2.36 (s, 3H), 4.12 (m, 2H), 4.59 (m, 2H), 7.39 (m, 1H), 7.83 (dt, J=7.96 Hz, 1.76 Hz, 1H), 7.94 (d, J=8.04 Hz, 1H), 8.60 (d, J=4.00 Hz, 1H), 10.24 (s, 1H, NH). MS: 235.1 [M+H]$^+$.

Example 7

(E)-N,N-dimethyl-2-(1-(pyridin-2-yl)ethylidene) hydrazine-1-carbothioamide (7)

Following General Method A for the condensation of N,N-dimethylhydrazinecarbothioamide and 1-(pyridin-2-yl)ethan-1-one the title compound 7 was isolated as a white solid after recrystallization from MeOH. MS: 223.1 [M+H]$^+$.

Example 8

(E)-N-methyl-2-(1-(pyridin-2-yl)ethylidene)hydrazine-1-carbothioamide (8)

Following General Method A for the condensation of N-methylhydrazinecarbothioamide and 1-(pyridin-2-yl)ethan-1-one the title compound 8 was isolated as a white solid after recrystallization from MeOH. $^1$H-NMR (400 MHz, DMSO-d$_6$) δ 2.39 (s, 3H), 3.07 (d, J=4.40 Hz, 3H), 7.40 (t, J=6.20 Hz, 1H), 7.82 (t, J=8.00 Hz, 1H), 8.43 (d, J=8.04 Hz, 1H), 8.59 (d, J=4.80 Hz, 1H), 8.64 (m, 1H, NH), 10.35 (s, 1H, NH). MS: 209.1 [M+H]$^+$.

Example 9

(E)-3,3-difluoro-N'-(1-(pyridin-2-yl)ethylidene)azetidine-1-carbothiohydrazide (9)

Following General Method A for the condensation of 3,3-difluoroazetidine-1-carbothiohydrazide and 1-(pyridin-2-yl)ethan-1-one the title compound 9 was isolated as a white solid after recrystallization from MeOH. $^1$H-NMR (400 MHz, DMSO-d$_6$) δ 1.19 (t, J=7.24 Hz, 2H), 2.47 and 2.54 (E/Z s, 3H), 4.52 (t, J=11.8 Hz, 2H), 7.47 (m, 1H), 7.89 (t, J=7.40 Hz, 1H), 8.09 (d, J=8.04 Hz, 1H), 8.63 (d, J=4.80 Hz, 1H), 9.71 (s, 1H, NH). MS: 271.1 [M+H]$^+$.

Example 10

(E)-N'-(1-(pyridin-2-yl)ethylidene)azetidine-1-carbohydrazide (10)

Azetidine (85 mg, 1.5 mmol) was dissolved in 5 mL methylene chloride and diisopropylethylamine (195 mg, 1.50 mmol, 1.0 equiv.) was added followed by triphosgene (267 mg, 0.9 mmol, 0.6 equiv.) and the reaction mixture stirred at ambient temperature for 4 h to generate the azetidine-1-carbonyl chloride in situ. Without workup, (E)-2-(1-hydrazonoethyl pyridine (203 mg, 1.5 mmol, 1.0 equiv.) was added directly to this mixture following by additional diisopropylethylamine 195 mg, 1.50 mmol, 1.0 equiv.) and the reaction continued to stir at ambient temperature for 72 h. The reaction was then evaporated to dryness and purified by silica gel chromatography (high purity grade silica gel, 32-64 microns, 230-400 mesh) eluted with a gradient of 5-10% methanol/methylene chloride with 1% triethylamine to give a white crystalline solid in selected middle fractions. These crystals were washed with 5:1 hexanes:methylene chloride, and dried under vacuum to give 24 mg of the title compound 10 as a free flowing white crystalline solid. $^1$H-NMR (400 MHz, CDCl$_3$) δ 2.28 (s, 3H), 2.32 (t, J=7.68 Hz, 1H), 2.36 (t, J=7.80 Hz, 1H), 4.35 (t, J=7.36 Hz, 4H), 7.24 (ddd, J=3.52 Hz, 2.48 Hz, 1.08 Hz, 1H), 7.66 (dt, J=7.84 Hz, 1.76 Hz, 1H), 7.81 (s, 1H, NH), 7.91 (d, J=8.08 Hz, 1H), 8.57 (d, J=4.20 Hz, 1H). MS: 219 [M+H]$^+$.

Example 11

(E)-N'-(2,2-dimethyl-1-(pyridin-2-yl)propylidene) azetidine-1-carbothiohydrazide (11)

Following General Method A for the condensation of azetidine-1-carbothiohydrazide and 2,2-dimethyl-1-(pyridin-2-yl)propan-1-one, the title compound 11 was isolated as a white solid after recrystallization from EtOAc/Hex. $^1$H-NMR (400 MHz, CDCl$_3$) δ 1.18 (s, 9H), 2.29 (t, J=7.76 Hz, 1H), 2.33 (t, J=7.84 Hz, 1H), 4.26 (t, J=7.36 Hz, 1H), 4.66 (t, J=7.72 Hz, 1H), 7.18 (d, J=7.76 Hz, 1H), 7.35 (ddd, J=6.00 Hz, 4.92 Hz, 1.12 Hz, 1H), 7.81 (dt, J=7.76 Hz, 1.76 Hz, 1H), 8.26 (br. s, 1H, NH), 8.76 (d, J=4.80 Hz, 1H). MS: 277.1 [M+H]$^+$.

Example 12

Synthesis of (12):

To a suspension of 6 (190.8 mg, 0.814 mmol, 1 equiv.) in EtOH (20 ml) was added ZnCl$_2$ (55.5 mg, 0.407 mmol, 0.5 equiv.). After 5 minutes, TEA (0.80 ml, excess) was added and the mixture was heated for 2 hours at reflux under nitrogen. Upon cooling to ambient temperature, a solid precipitated that was collected by filtration and washed with EtOH followed by Et$_2$O. The solids were dried under high vacuum to give [Zn(ZMCl)$_2$] 12, (215 mg, 0.404 mmol, 99%) as a bright yellow solid. $^1$H-NMR (400 MHz, DMSO-d$_6$) δ 2.26 (overlapping tt, J=7.48 Hz, 7.40 Hz, 4H), 2.58 (s, 6H), 4.05 (m, 8H), 7.29 (dd, J=7.28 Hz, 5.60 Hz, 2H), 7.75 (m, 4H), 7.88 (dt, J=8.04 Hz, 1.52 Hz, 2H). Slow evaporation of [Zn(ZMCl)$_2$] from a 1:1 mixture of DCM/MeOH afforded yellow crystals that were suitable for X-ray crystallography. See X-ray ORTEP drawing (FIG. 1) and data tables.

Cell-based TOV112D activity for representative compounds is shown in Table 1.

TABLE 1

| COMPOUND Number | Structure | Activity TOV112D |
|---|---|---|
| 1 | ![structure] | +++ |
| 2 | ![structure] | +++ |
| 6 | ![structure] | +++ |
| 7 | ![structure] | +++ |
| 9 | ![structure] | +++ |
| 10 | ![structure] | + |

TABLE 1-continued

| COMPOUND Number | Structure | Activity TOV112D |
|---|---|---|
| 11 | | + |
| 12 | | +++ |

+++, most active;
++, moderately active;
+, less active

Example 13

Figure 5:
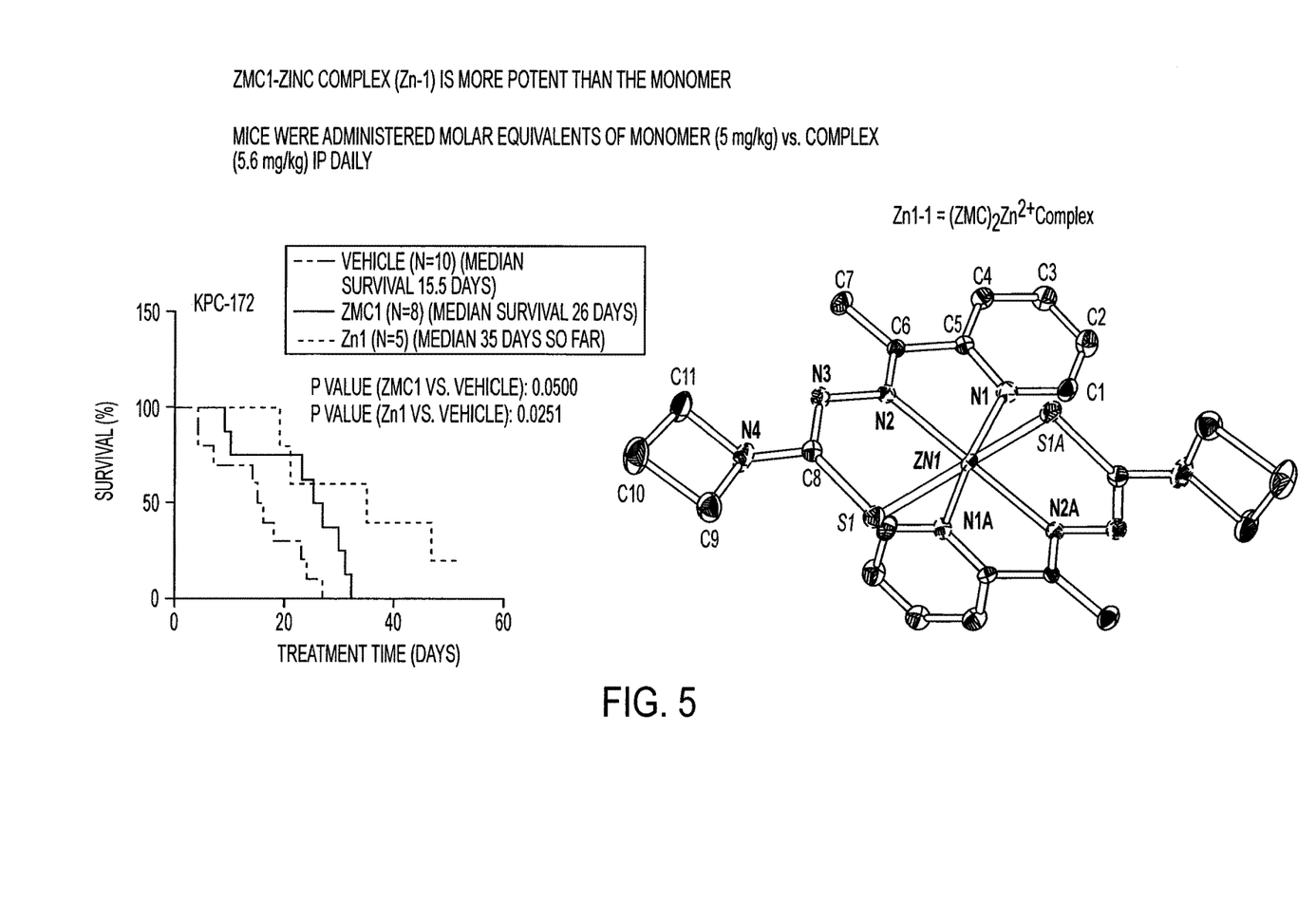
FIG. 5 illustrates data from Example 13 demonstrating that the Zinc (II) complex ZN1 exhibits greater potency over the monomeric form ZMCl in vivo.

Mice were administered molar equivalents of monomer ZMCl (5 mg/kg) versus complex ZN1 (5.6 mg/kg) IP daily and monitored for survival. Results are shown in FIG. 5.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A complex comprising $Zn^{2+}$ and a compound of formula (I):

(I)

or an ion or poly-ion thereof, wherein:
  n is 0, 1, 2, 3, or 4;
  Y is O, S, or Se;
  each $R^1$ is independently selected from $(C_1-C_4)$alkyl, $(C_1-C_4)$alkoxy, hydroxyl, and halo;
  $R^2$ is selected from the group consisting of H and $(C_1-C_6)$alkyl that is optionally substituted with aryl; and
  $R^a$ and $R^b$ taken together with the nitrogen to which they are attached form a 4-, 5-, or 6-membered heterocycle that is optionally substituted with one to three substituents independently selected from $(C_1-C_4)$alkyl, $(C_1-C_4)$alkoxy, hydroxyl, halo, aryl, and heteroaryl;
or a solvate thereof.

2. The complex of claim 1 wherein:
  n is 0;
  $R^2$ is $(C_1-C_4)$alkyl;
  Y is S or Se; and
  $R^a$ and each $R^b$ taken together with the nitrogen to which they are attached form a heterocycle selected from:

or a solvate thereof.

3. The complex of claim 1 that comprises a compound selected from the group consisting of:

and ions and poly-ions thereof or a solvate thereof.

4. The complex of claim 1 wherein the ratio of the number of compounds of formula (I) or ions or poly-ions thereof to zinc Zn' ions is about 2:1; or a solvate thereof.

5. The complex of claim 4 that comprises a compound selected from the group consisting of:

and ions and poly-ions thereof, wherein: the ratio of the compound or ion or poly-ion to Zn$^{2+}$ is about 2:1; or a solvate thereof.

6. A neutral coordination complex comprising Zn$^{2+}$ and a compound selected from the group consisting of:

and ions and poly-ions thereof, wherein: the ratio of the compound or ion or poly-ion to Zn$^{2+}$ is about 2:1; or a solvate thereof.

7. The complex:

or a solvate thereof.

8. A pharmaceutical composition, comprising a complex of claim 1 or a solvate thereof, and a pharmaceutically acceptable carrier.

9. An injectable pharmaceutical formulation comprising, a complex of claim 1 or a solvate thereof, and a pharmaceutically acceptable carrier.

10. A pharmaceutical composition, comprising a complex of claim 6 or a solvate thereof, and a pharmaceutically acceptable carrier.

11. A pharmaceutical composition, comprising a complex of claim 7 or a solvate thereof, and a pharmaceutically acceptable carrier.

* * * * *

UNITED STATES PATENT AND TRADEMARK OFFICE
CERTIFICATE OF CORRECTION

PATENT NO. : 10,221,133 B2
APPLICATION NO. : 15/545966
DATED : March 5, 2019
INVENTOR(S) : David J. Augeri et al.

Page 1 of 1

It is certified that error appears in the above-identified patent and that said Letters Patent is hereby corrected as shown below:

In the Claims

Column 16, Line 67, Claim 4, delete "zinc Zn' ions is about" and insert -- zinc $Zn^{2+}$ ions is about -- therefor.

Signed and Sealed this
Seventeenth Day of September, 2019

Andrei Iancu
*Director of the United States Patent and Trademark Office*